US006787130B2

(12) United States Patent
Dhamdhere et al.

(10) Patent No.: US 6,787,130 B2
(45) Date of Patent: Sep. 7, 2004

(54) HAIR TREATMENT COMPOSITIONS WHICH PROVIDE HAIR BODY AND WHICH COMPRISE SILICON PRESSURE SENSITIVE ADHESIVES

(75) Inventors: Mrunalini Dhamdhere, Des Plaines, IL (US); Trefor A. Evans, Lombard, IL (US); Yun Shan, Mundelein, IL (US); Pawel Milczarek, Schaumburg, IL (US); Cheryl Taylor, Merseyside (GB); Elena Barbuzzi, Wirral (GB); Stephen Wire, Wirral (GB); Wolfgang Robert Bergmann, Long Grove, IL (US)

(73) Assignee: Unilever Home & Personal Care USA a division of Conopco, Inc., Greenwich, CT (US)

(*) Notice: Subject to any disclaimer, the term of this patent is extended or adjusted under 35 U.S.C. 154(b) by 0 days.

(21) Appl. No.: 09/968,214

(22) Filed: Oct. 1, 2001

(65) Prior Publication Data

US 2003/0091523 A1 May 15, 2003

(51) Int. Cl.[7] .......................... A61K 7/06; A61K 7/075; A61K 7/00
(52) U.S. Cl. ................... 424/70.12; 424/401; 424/70.1; 424/70.27; 424/70.28
(58) Field of Search ........................... 424/401, 70.1–74

(56) References Cited

U.S. PATENT DOCUMENTS

| | | | |
|---|---|---|---|
| 5,060,804 | 10/1991 | Beales et al. ................. | 310/81 |
| 5,209,924 | 5/1993 | Garbe et al. ............. | 424/70.11 |
| 5,337,047 | 8/1994 | Myers ......................... | 340/945 |
| 5,451,610 | * 9/1995 | Krzysik ....................... | 424/59 |
| 5,776,444 | * 7/1998 | Birtwistle et al. ....... | 424/70.12 |
| 5,968,286 | 10/1999 | Crudele et al. .............. | 134/42 |
| 6,524,598 | * 2/2003 | Sunkel et al. .............. | 424/401 |

FOREIGN PATENT DOCUMENTS

| | | |
|---|---|---|
| EP | 0376533 | 7/1990 |
| EP | 0412707 A1 | 2/1991 |
| EP | 0412770 A | 2/1991 |
| EP | 0412771 A1 | 2/1991 |
| EP | 0610015 A | 8/1994 |
| WO | 93/23446 | 11/1993 |

OTHER PUBLICATIONS

International Search Report Application No. PCT/EP 02/10643 mailed Feb. 18, 2003.

* cited by examiner

Primary Examiner—Shengjun Wang
(74) Attorney, Agent, or Firm—Karen E. Klumas

(57) ABSTRACT

An aqueous hair treatment composition comprising:

a) at least one silicone pressure sensitive adhesive; and
b) at least one material selected from the group consisting of a hair conditioning agent, a hair cleansing agent, and an agent for hair care suspension, is described.

16 Claims, 4 Drawing Sheets

HAIR TREATMENT COMPOSITIONS WHICH PROVIDE HAIR BODY AND WHICH COMPRISE SILICON PRESSURE SENSITIVE ADHESIVES

FIELD OF THE INVENTION

This invention relates to rinse-off hair treatment compositions and to their use in the treatment of hair.

BACKGROUND AND PRIOR ART

Shampoo compositions are generally formulated with highly effective cleansing surfactants, typically anionic surfactants, and do not in themselves provide much conditioning or styling benefit to the hair. In fact, basic shampoo formulations which have not been supplemented with specific conditioning or styling agents have a tendency to leave the hair in a cosmetically-unsatisfactory condition with regards to manageability and stylability. The hair tends to have a harsh, dull and dry feel, often referred to as "creak", is often difficult to comb, in either the wet or the dry state, typically has poor brushing properties, and tends to have poor set-retaining abilities.

This has resulted in the use of products containing specific conditioning and/or styling agents. Such agents are generally applied separately after shampooing and rinsing the hair, for example, in the form of conditioner formulations or styling mousses etc. Alternatively, conditioning and/or styling agents have been incorporated into the shampoo formulations. Although the latter approach provides the advantage of removing the need for a separate conditioner or styling treatment, the conditioning and/or styling agents are not always compatible with the shampoo ingredients, especially the anionic surfactant. This can result in the cleansing action and/or cosmetic benefit being compromised.

One of the most common methods for imparting styling benefits to the hair has been the use of hair fixative agents, such as high molecular weight polymers. The problem with using such agents is that they have a tendency to negatively impact on conditioning attributes such as wet and dry stage clean feel and smoothness. In fact, they can result in a sticky feel to the hair.

Conventional styling polymers are typically water soluble. This means that when incorporated into a shampoo or conditioner which is rinsed off the hair, there is a tendency for the styling polymer to be washed away to a greater or lesser degree with the shampoo/conditioner. Hence, most styling products are leave-in products which are applied to the hair as post-shampoo/conditioner treatments.

The problem being addressed by the present invention is the provision of rinse-off hair treatment compositions which impart styling benefits, and in particular body benefits on the hair, but which do not compromise the cleansing action of the shampoo and which do not negatively impact on the conditioning attributes of the hair. The body benefits or attributes the present invention is looking particularly to provide include root lift, increased hair volume, bounce, control (i.e. ease of styling) and manageability, i.e. maintenance of style without undue stiffness and negative sensory feel. Such body attributes are particularly attractive to people with fine or long, weighty hair.

One way in which this problem has been addressed in the past has been to include conditioning agents, for example silicones and cationic surfactants, in the compositions, to counter the negative effects of the styling agents. Although such conditioning agents do provide substantial improvements in for example the wet and dry combing properties of the hair and in the smoothness of the hair, they tend to have a negative effect on many of the attributes associated with hair body.

An alternative approach has been the use different forms of styling agents such as small particulate materials. Such an approach is described, for example, in our unpublished PCT International Patent Application No. PCT/GB00/04020. This document describes the use of small hard particles, and in particular colloidal silica, in hair treatment compositions to impart body and volume to the hair. Although providing significant styling benefits, the use of these materials can still lead to small levels of sensory negatives, such as for example a dry feel to the hair.

JP 10144622 (Toshiba Silicone) discloses cosmetic compositions containing particles consisting of colloidal silica cores surrounded by silicone shells which may be used on the skin or hair. Hairdressing lotions, hair creams and cleansing compositions such as a shampoo, rinse and conditioner are disclosed as suitable cosmetic compositions in which the particles can be utilized.

We have now found that the inclusion of a certain level of silicone pressure sensitive adhesives (silicone PSA) in the hair treatment formulations provides substantial styling go benefits, in particular with regards to imparting body attributes to the hair. Furthermore, the conditioning attributes of the hair are not adversely affected by the use of hair compositions containing these silicone PSA's and there is no necessity to incorporate additional conditioning agents or specialized surfactant systems. The compositions of the present invention are also stable.

The incorporation of silicone PSA's into the hair treatment compositions of this invention leads to substantive improvements in the body of the washed and optionally conditioned hair, especially if a subsequent styling regime is followed. The compositions impart body attributes, such as root lift, volume, bounce and manageability, in the absence (or substantial absence) of a styling polymer, which leads to compositions which have a styling benefit, but nevertheless do not suffer from the sensory negatives (e.g. stickiness and/or dry feel) which are associated with prior styling compositions which are based on, for example, a styling polymer.

SUMMARY OF THE INVENTION

Accordingly, this invention provides an aqueous hair treatment composition comprising:
a) at least one silicone pressure sensitive adhesive
b) a material selected from the group consisting of a suspending agent, a hair conditioning agent and a hair cleansing agent.

Preferably, the resulting hair care composition will increase static friction of dry hair by at least about 10%, and will increase in the dynamic friction of dry hair by no more than 100% or leave said dynamic friction unchanged or decrease said dynamic friction. This invention provides for the use of silicone PSA's as defined herein in a hair treatment composition to impart body without compromising conditioning.

BRIEF DESCRIPTION OF THE DRAWING

The invention is further described with the following drawing in which.

DETAILED DESCRIPTION OF THE INVENTION

Figure 1:
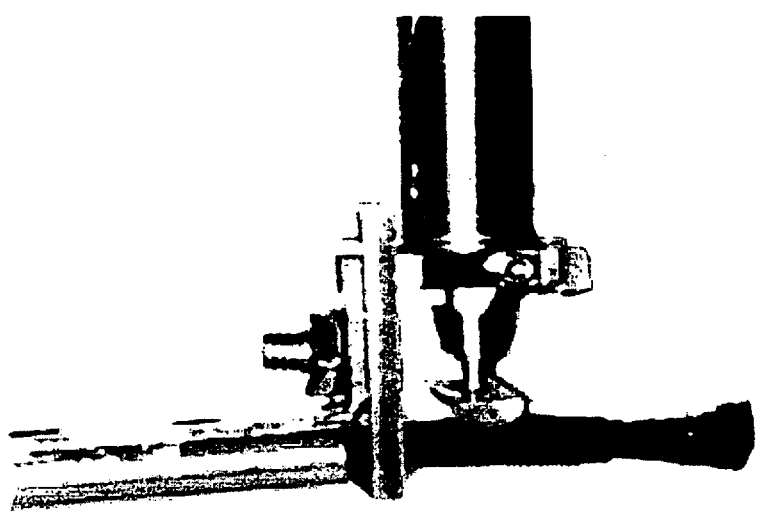
FIG. 1 is a pictorial of our test instrument measuring static and dynamic force.

Unless specified otherwise, all wt % values quoted hereinafter are percentages by weight based on total weight of the hair treatment composition.

Compositions of the invention may be prepared by known methods, or may be prepared by methods which are analogous to known methods.

By "insoluble" is meant that the material is not soluble in water (distilled or equivalent) at a concentration of 0.1%, at 25° C.

The invention provides an aqueous hair treatment composition comprising:

a) at least one silicone pressure sensitive adhesive
b) a material selected from the group consisting of a suspending agent, a hair conditioning agent and a hair cleansing agent.

Preferably, the resulting hair care composition will increase static friction of dry hair by at least 10%, or more preferably by at least about 15%, most preferably by about 20% and which increases the dynamic friction of dry hair by not more than 100%, or more preferably no more than by 60% or most preferably not more than by 40% Said dynamic friction of dry hair may also be unchanged or decrease.

More preferably, the invention provides an aqueous hair treatment composition comprising a) about 0.1% to about 10% of at least one silicone pressure sensitive adhesive; and
b1) about 0.1% to about 10% of at least one suspending agent; or
b2) about 0.05% to about 10% of at least one hair conditioning agent; or
b3) about 5% to about 40% of at least one hair cleansing agent.

What follows now are descriptions of the materials and ingredients that may be employed in the compositions of the present invention.

Silicone Pressure Sensitive Adhesives

Pressure sensitive adhesives (PSA) are being used for a wide variety of adhesive applications. Organic PSAs have been finding increased utility principally for manufacture of adhesive tapes and labels. Other PSA uses include automotive, medical and coating industry applications. There are several chemical types of PSAs, including tackified natural rubbers, synthetic rubbers, polyvinyl ether types PSAs, acrylic, and silicone PSAs. The present invention relates to the use of Silicone PSAs in hair care applications.

PSAs require a delicate balance of viscous and elastic properties that results in desired balance of adhesion, cohesion, peel strength and elasticity. The performance of PSA is governed mainly by three properties: Tack, peel strength and shear strength. Properties such as shear strength, cohesion can be tested using standard tests that are found in the detail in literature (Ref A. Zosel, *J. Adhesion,* 1994, 44, pp 1–6). Adhesion is the binding force between two different materials, whereas cohesion is the binding force between two similar materials. When two materials are brought into contact with each other, the surface molecules interact, giving rise to attractive forces that may be physical, chemical or electrostatic (corresponding to adsorption, covalent bonding or van der Waals forces, respectively). When the molecules are similar, as in the case of two 'glue molecules,' the cohesive force causes the glue to stick to itself. When the molecules are dissimilar, as in the case of a glue molecule and a molecule of the substrate (the surface the glue is sticking to), the adhesive force holds the glue to the substrate. PSAs usually consist of chemical moieties that exhibit varying tackifying and elastomeric behaviors. By controlling the amount of the viscous and elastic materials, desired properties can be obtained. As used herein, the term PSA shall refer to an adhesive composition that satisfies the Dahlquist criterion, i.e.: 1 -sec creep compliance greater than $1\times10^{-6}$ cm$^2$/dyne (Ref. Handbook of Pressure Sensitive Adhesive Technology, p 172, D. Satas (ed.) Van Nostrand, N.Y. (1989)). Typically, a pressure sensitive adhesive is normally tacky at room temperature and adheres to a surface upon contact to the surface without the need for more than finger or hand pressure. Owing to the unique chemistry of PSAs, they exhibit some unique properties such as low glass transition temperature ($T_g$), low surface energy, high flexibility, quick bonding.

This present invention relates to the use of silicone PSAs for hair care rinse-off applications. Silicone PSAs comprise two major components, a polymer or gum, and a tackifying resin. The polymer is typically a high molecular weight polydimethylsiloxane or polydimethyldiphenylsiloxane, that contains residual silanol functionality (SiOH) on the ends of the polymer chain, or a block copolymer comprising polydiorganosiloxane soft segments and urea terminated hard segments. The tackifying resin is generally a three dimensional silicate structure that is endcapped with trimethylsiloxy groups (OsiMe$_3$) and also contains some residual silanol functionality. Manufacture of typical silicone PSA is described in U.S. Pat. No. 2,736,721 (Dexter). Other materials can be added for special purposes, including pigments, plasticizers, and fillers. Although, silicone PSAs have been cited in U.S. Pat. No. 5,330,747, U.S. Pat. No. 5,460,804 and U.S. Pat. No. 5,451,610.

A preferable silicone PSA can be a mixture of a hydroxy-terminated polydimethylsiloxane gum of $T_g$ below –20° C. with a silicone resin which has a $T_g$ or softening point above 0° C. The gum is lightly crosslinked with the resin. The resin comprises at least 30% units selected from RSiO3/2 units (T units) and SiO4/2 units (Q units), optionally together with R3SiO1/2 units (M units) and/or R2SiO2/2 units (D units), where R is a monovalent hydrocarbon radical, preferably methyl, and generally has an average of at least one R group per Si atom. The $T_g$ of the blend of resin and gum is generally between –15 and 15° C. (T at tan delta maximum). The resin lowers the rubbery plateau modulus of the system. The resin is preferably a silanol-containing trimethylated silicate resin, that is a resin comprising Q and M units in which some trimethylsilyl groups are replaced by dimethylhydroxysilyl groups. The PSAs described above can be supplied as solutions or in emulsified form to be used in the hair care compositions of this invention.

A preferred silicone PSA emulsion can be prepared by mixing the silicone PSA in volatile silicone fluid. The silicone PSA together with a volatile silicone fluid having a boiling point below 300° C. is emulsified together in water using one or more surfactants. The preferred surfactants are anionic or nonionic surfactants, especially a blend of anionic and nonionic surfactants. The silicone fluid can be a linear polydiorganosiloxane such as hexamethyldisiloxane, octamethyltrisiloxane, decamethyltetrasiloxane, dodecamethylpentasiloxane or a polydimethylsiloxane of viscosity 1cSt, or can be a cyclic siloxane such as decamethylcyclopentasiloxane or octamethylcyclotetrasiloxane or can be a mixture of one or more linear polydimethylsiloxanes with one or more cyclic siloxanes.

Silicone PSAs may be formed with a wide range of tack properties, peel adhesion properties and cohesion properties. In the hair care compositions of the present invention, it is also preferable that the silicone PSAs have tack and adhesion properties in the following range:

|  | Tack (g) | Adhesion (g/cm) |
| --- | --- | --- |
| Low tack (LT) | <70 | 800 |
| Medium tack (MT) | 70 | 600 |
| High tack (HT) | 500 | 400 |

In the hair care compositions of the present invention, it is also preferable that the silicone PSAs have tack properties between about 40 g to about 750 g, or more preferably 50 g to 600 g; adhesion properties between about 1600 g/cm to 200 g/cm, or more preferably 1000 g/cm to 300 g/cm.

Silicone PSA that may be used in the compositions of the invention may have a resin-to-polymer ratio that can range from about 25 to 75 to about 75 to 25, more preferably from about 55 to 45 to 65 to 35.

In the hair care compositions of the present invention, the silicone PSAs can cause said compositions to maximally increase the dynamic friction of dry hair by 100% or 60%, or most preferably by 40%; and can cause the static friction of dry hair to increase by at least 10% or 15%, or most preferably by 20%.

This invention does not include the silicone acrylate type of PSAs, such as acrylate dimethicone copolymer cited in U.S. Pat. No. 5,166,276 or acrylates/dimethicone methacrylate copolymer that have been previously used in hair care applications.

Hair Treatment Compositions

Compositions in accordance with the invention may be formulated as compositions for the treatment of hair and subsequent rinsing.

Compositions Made With a Suspending Agent

Compositions in accordance with this invention may also be formulated as suspensions for the treatment of hair and subsequent rinsing. These compositions will require silicone PSAs and a suspending agent.

Suspending Agents

In a preferred embodiment, the hair treatment composition further comprises from 0.01 to 10 wt % of a suspending agent for the silicone pressure sensitive adhesive. Suitable suspending agents are selected from polyacrylic acids, cross-linked polymers of acrylic acid, copolymers of acrylic acid with a hydrophobic monomer, copolymers of carboxylic acid-containing monomers and acrylic esters, cross-linked copolymers of acrylic acid and acrylate esters, heteropolysaccharide gums and crystalline long chain acyl In derivatives. The long chain acyl derivative is desirably selected from ethylene glycol stearate, alkanolamides of fatty acids having from 16 to 22 carbon atoms and mixtures thereof. Ethylene glycol distearate and polyethylene glycol 3 distearate are preferred long chain acyl derivatives. Polyacrylic acid is available commercially as Carbopol 420, Carbopol 488 or Carbopol 493. Polymers of acrylic acid cross-linked with a polyfunctional agent may also be used, they are available commercially as Carbopol 910, Carbopol 934, Carbopol 940, Carbopol 941 and Carbopol 980. An example of a suitable copolymer of a carboxylic acid containing a monomer and acrylic acid esters is Carbopol 1342. All Carbopol (trade mark) materials are available from Goodrich.

Suitable cross-linked polymers of acrylic acid and acrylate esters are Pemulen TR1 or Pemulen TR2. A suitable heteropolysaccharide gum is xanthan gum, for example that available as Kelzan mu.

Compositions Made With a Conditioning Agent

Compositions in accordance with this invention may also be formulated as conditioners for the treatment of hair typically after shampooing and subsequent rinsing. These compositions will require silicone PSAs and a conditioning agent.

Conditioning Agents

Such a conditioner will comprise at least one silicone pressure sensitive adhesive and one or more conditioning agents that are cosmetically acceptable and suitable for topical application to the hair.

Suitable conditioning agents are selected from cationic surfactants, used singly or in admixture.

Cationic surfactants useful in compositions of the invention contain amino or quaternary ammonium hydrophilic moieties which are positively charged when dissolved in the aqueous composition of the present invention.

Examples of suitable cationic surfactants are those corresponding to the formula:

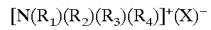

$[N(R_1)(R_2)(R_3)(R_4)]^+(X)^-$ in which $R_1$, $R_2$, $R_3$, and $R_4$ are independently selected from (a) an aliphatic group of from 1 to 22 carbon atoms, or (b) an aromatic, alkoxy, polyoxyalkylene, alkylamido, hydroxyalkyl, aryl or alkylaryl group having up to 22 carbon atoms; and X is a salt-forming anion such as those selected from halogen, (e.g. chloride, bromide), acetate, citrate, lactate, glycolate, phosphate nitrate, sulphate, and alkylsulphate radicals.

The aliphatic groups can contain, in addition to carbon and hydrogen atoms, ether linkages, and other groups such as amino groups. The longer chain aliphatic groups, e.g., those of about 12 carbons, or higher, can be saturated or unsaturated.

The most preferred cationic surfactants for conditioner compositions of the present invention are monoalkyl quaternary ammonium compounds in which the alkyl chain length is C8 to C14.

Suitable examples of such materials correspond to the formula:

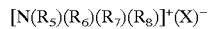

$[N(R_5)(R_6)(R_7)(R_8)]^+(X)^-$ in which $R_5$ is a hydrocarbyl chain having 8 to 14 carbon atoms or a functionalized hydrocarbyl chain with 8 to 14 carbon atoms and containing ether, ester, amido or amino moieties present as substituents or as linkages in the radical chain, and $R_6$, $R_7$ and $R_8$ are independently selected from (a) hydrocarbyl chains of from 1 to about 4 carbon atoms, or (b) functionalized hydrocarbyl chains having from 1 to about 4 carbon atoms and containing one or more aromatic, ether, ester, amido or amino moieties present as substituents or as linkages in the radical chain, and X is a salt-forming anion such as those selected from halogen, (e.g. chloride, bromide), acetate, citrate, lactate, glycolate, phosphate nitrate, sulphate, and alkylsulphate radicals.

The functionalised hydrocarbyl chains (b) may suitably contain one or more hydrophilic moieties selected from alkoxy (preferably $C_1$–$C_3$ alkoxy), polyoxyalkylene (preferably $C_1$–$C_3$ polyoxyalkylene), alkylamido, hydroxyalkyl, alkylester, and combinations thereof.

Preferably the hydrocarbyl chains $R_1$ have 12 to 14 carbon atoms, most preferably 12 carbon atoms. They may be derived from source oils which contain substantial amounts of fatty acids having the desired hydrocarbyl chain length. For example, the fatty acids from palm kernel oil or coconut oil can be used as a source of C8 to C12 hydrocarbyl chains.

Typical monoalkyl quaternary ammonium compounds of the above general formula for use in shampoo compositions of the invention include:

(i) lauryl trimethylammonium chloride(available commercially as Arquad C35 ex-Akzo); cocodimethyl benzyl ammonium chloride (available commercially as Arquad DMCB-80 ex-Akzo)

(ii) compounds of the formula:

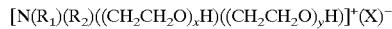

wherein:

x+y is an integer from 2 to 20;

$R_1$ is a hydrocarbyl chain having 8 to 14, preferably 12 to 14, most preferably 12 carbon atoms or a functionalised hydrocarbyl chain with 8 to 14, preferably 12 to 14, most preferably 12 carbon atoms and containing ether, ester, amido or amino moieties present as substituents or as linkages in the radical chain;

$R_2$ is a $C_1$–$C_3$ alkyl group or benzyl group, preferably methyl, and

X is a salt-forming anion such as those selected from halogen, (e.g. chloride, bromide), acetate, citrate, lactate, glycolate, phosphate nitrate, sulphate, methosulphate and alkylsulphate radicals.

Suitable examples are PEG-n lauryl ammonium chlorides (where n is the PEG chain length), such as PEG-2 cocomonium chloride (available commercially as Ethoquad C12 ex-Akzo Nobel); PEG-2 cocobenzyl ammonium chloride (available commercially as Ethoquad CB/12 ex-Akzo Nobel); PEG-5 cocomonium methosulphate (available commercially as Rewoquat CPEM ex-Rewo); PEG-15 cocomonium chloride (available commercially as Ethoquad C/25 ex-Akzo)

(iii) compounds of the formula:

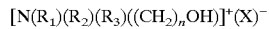

wherein:

n is an integer from 1 to 4, preferably 2;

$R_1$ is a hydrocarbyl chain having 8 to 14, preferably 12 to 14, most preferably 12 carbon atoms;

$R_2$ and $R_3$ are independently selected from $C_1$–$C_3$ alkyl groups, and are preferably methyl, and $X^-$ is a salt-forming anion such as those selected from halogen, (e.g. chloride, bromide), acetate, citrate, lactate, glycolate, phosphate nitrate, sulphate, and alkylsulphate radicals.

Suitable examples are lauryldimethylhydroxyethylammonium chloride (available commercially as Prapagen HY ex-Clariant)

Mixtures of any of the foregoing cationic surfactants compounds may also be suitable.

Examples of suitable cationic surfactants include:

quaternary ammonium chlorides, e.g. alkyltrimethylammonium chlorides wherein the alkyl group has from about 8 to 22 carbon atoms, for example octyltrimethylammonium chloride, dodecyltrimethylammonium chloride, hexadecyltrimethylammonium chloride, cetyltrimethylammonium chloride, octyldimethylbenzylammonium chloride, decyldimethylbenzylammonium chloride, stearyldi-methylbenzylammonium chloride, didodecyldimethylammonium chloride, dioctadecyldimethylammonium chloride, tallow trimethylammonium chloride, cocotrimethylammonium chloride, and the corresponding salts thereof, e.g., bromides, hydroxides. Cetylpyridinium chloride or salts thereof, e.g., chloride Quaternium-5
Quaternium-31
Quaternium-18 and mixtures thereof.

In the conditioners of the invention, the level of cationic surfactant is preferably from 0.01 to 10, more preferably 0.05 to 5, most preferably 0.1 to 2 wt % of the total composition.

Optional Conditioning Materials

Fatty Alcohol Material

Conditioner compositions of the invention preferably additionally comprise a fatty alcohol material. The combined use of fatty alcohol materials and cationic surfactants in conditioning compositions is believed to be especially advantageous, because this leads to the formation of a lamellar phase, in which the cationic surfactant is dispersed.

By "fatty alcohol material" is meant a fatty alcohol, an alkoxylated fatty alcohol, or a mixture thereof.

Representative fatty alcohols comprise from 8 to 22 carbon atoms, more preferably 16 to 20. Examples of suitable fatty alcohols include cetyl alcohol, stearyl alcohol and mixtures thereof. The use of these materials is also advantageous in that they contribute to the overall conditioning properties of compositions of the invention.

Alkoxylated, (e.g. ethoxylated or propoxylated) fatty alcohols having from about 12 to about 18 carbon atoms in the alkyl chain can be used in place of, or in addition to, the fatty alcohols themselves. Suitable examples include ethylene glycol cetyl ether, polyoxyethylene (2) stearyl ether, polyoxyethylene (4) cetyl ether, and mixtures thereof.

The level of fatty alcohol material in conditioners of the invention is suitably from 0.01 to 15, preferably from 0.1 to 10, and more preferably from 0.1 to 5 wt %. The weight ratio of cationic surfactant to fatty alcohol is suitably from 10:1 to 1:10, preferably from 4:1 to 1:8, optimally from 1:1 to 1:7, for example 1:3.

Cationic Polymers

Conditioner compositions of the invention can also contain a cationic polymer. Suitable cationic polymers are described hereinbelow in relation to shampoo compositions.

Compositions Made with a Hair Cleansing Agent (Shampoo Compositions)

A particularly preferred hair treatment composition in accordance with the invention is a shampoo composition that comprises of at least one silicone PSA and at least one cleansing agent.

Such a shampoo composition will comprise at least one silicone pressure sensitive adhesive and one or more cleansing surfactants which are cosmetically acceptable and suitable for topical application to the hair. Further surfactants may be present as an additional ingredient if sufficient for cleansing purposes is not provided as emulsifier for the silicone component. It is preferred that shampoo compositions of the invention comprise at least one further surfactant (in addition to that used as emulsifying agent for the silicone component) to provide a cleansing benefit.

Suitable cleansing agents, which may be used singularly or in combination, are selected from anionic, nonionic, amphoteric and zwitterionic surfactants, and mixtures thereof. The cleansing agent may be the same surfactant as the emulsifier, or may be different.

Cleansing Agents
Anionic Cleansing Surfactant

Shampoo compositions according to the invention will typically comprise one or more anionic cleansing surfactants which are cosmetically acceptable and suitable for topical application to the hair.

Examples of suitable anionic cleansing surfactants are the alkyl sulphates, alkyl ether sulphates, alkaryl sulphonates, alkanoyl isethionates, alkyl succinates, alkyl sulphosuccinates, N-alkyl sarcosinates, alkyl phosphates, alkyl ether phosphates, alkyl ether carboxylates, and alpha-olefin sulphonates, especially their sodium, magnesium, ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from 1 to 10 ethylene oxide or propylene oxide units per molecule.

Typical anionic cleansing surfactants for use in shampoo compositions of the invention include sodium oleyl succinate, ammonium lauryl sulphosuccinate, ammonium lauryl sulphate, sodium dodecylbenzene sulphonate, triethanolamine dodecylbenzene sulphonate, sodium cocoyl isethionate, sodium lauryl isethionate and sodium N-lauryl sarcosinate. The most preferred anionic surfactants are sodium lauryl sulphate, sodium lauryl ether sulphate(n)EO, (where n ranges from 1 to 3), ammonium lauryl sulphate and ammonium lauryl ether sulphate(n)EO, (where n ranges from 1 to 3).

Mixtures of any of the foregoing anionic cleansing surfactants may also be suitable.

The total amount of anionic cleansing surfactant in shampoo compositions of the invention is generally from 5 to 30, preferably from 6 to 20, more preferably from 8 to 16 wt %.

Amphoteric Surfactants

The shampoo composition can include other cleansing agents, to help impart aesthetic, physical or cleansing properties to the composition.

A preferred example is an amphoteric or zwitterionic surfactant, which can be included in an amount ranging from 0 to about 8, preferably from 1 to 4 wt %.

Examples of amphoteric and zwifterionic surfactants include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates, alkyl amidopropyl hydroxysultaines, acyl taurates and acyl glutamates, wherein the alkyl and acyl groups have from 8 to 19 carbon atoms. Typical amphoteric and zwitterionic surfactants for use in shampoos of the invention include lauryl amine oxide, cocodimethyl sulphopropyl betaine and preferably lauryl betaine, cocamidopropyl betaine and sodium cocamphopropionate.

Nonionic Surfactants

Another preferred example is a nonionic surfactant, which can be included in an amount ranging from 0 to 8, preferably from 2 to 5 wt %.

For example, representative nonionic surfactants that can be included in shampoo compositions of the invention include condensation products of aliphatic ($C_8$–$C_{18}$) primary or secondary linear or branched chain alcohols or phenols with alkylene oxides, usually ethylene oxide and generally having from 6 to 30 ethylene oxide groups.

Other representative nonionic surfactants include mono- or di-alkyl alkanolamides. Examples include coco mono- or di-ethanolamide and coco mono-isopropanolamide.

Further nonionic surfactants which can be included in shampoo compositions of the invention are the alkyl polyglycosides (APGs). Typically, the APG is one which comprises an alkyl group connected (optionally via a bridging group) to a block of one or more glycosyl groups. Preferred APGs are defined by the following formula:

$$RO\text{-}(G)_n$$

wherein R is a branched or straight chain alkyl group which may be saturated or unsaturated and G is a saccharide group. R may represent a mean alkyl chain length of from about $C_5$ to about $C_{20}$. Preferably R represents a mean alkyl chain length of from about $C_8$ to about $C_{12}$. Most preferably the value of R lies between about 9.5 and about 10.5. G may be selected from $C_5$ or $C_6$ monosaccharide residues, and is preferably a glucoside. G may be selected from the group comprising glucose, xylose, lactose, fructose, mannose and derivatives thereof Preferably G is glucose.

The degree of polymerization, n, may have a value of from about 1 to about 10 or more. Preferably, the value of n lies in the range of from about 1.1 to about 2. Most preferably the value of n lies in the range of from about 1.3 to about 1.5.

Suitable alkyl polyglycosides for use in the invention are commercially available and include for example those materials identified as: Oramix NS10 ex Seppic; Plantaren 1200 and Plantaren 2000 ex Henkel.

Other sugar-derived nonionic surfactants which can be included in shampoo compositions of the invention include the $C_{10}$–$C_{18}$ N-alkyl ($C_1$–$C_6$) polyhydroxy fatty acid amides, such as the $C_{12}$–$C_{18}$ N-methyl glucamides, as described for example in WO 92 06154 and U.S. Pat. No. 5,194,639, and the N-alkoxy polyhydroxy fatty acid amides, such as $C_{10}$–$C_{18}$ N-(3-methoxypropyl) glucamide.

Optional Shampoo Ingredients
Cationic Surfactants

The shampoo composition can also optionally include one or more cationic co-surfactants included in an amount ranging from 0.01 to 10, more preferably from 0.05 to 5, most preferably from 0.05 to 2 wt %. Useful cationic surfactants are described hereinabove in relation to conditioner compositions.

The total amount of surfactant (including any co-surfactant, and/or any emulsifier) in shampoo compositions of the invention is generally from 5 to 50, preferably from 5 to 30, more preferably from 10 to 25 wt %.

Cationic Polymer

A cationic polymer is a preferred ingredient in shampoo compositions of the invention, for enhancing conditioning performance of the shampoo.

The cationic polymer may be a homopolymer or be formed from two or more types of monomers. The molecular weight of the polymer will generally be between 5 000 and 10,000,000, typically at least 10 000 and preferably in the range 100 000 to about 2,000,000. The polymers will have cationic nitrogen containing groups such as quaternary ammonium or protonated amino groups, or a mixture thereof.

The cationic nitrogen-containing group will generally be present as a substituent on a fraction of the total monomer units of the cationic polymer. Thus when the polymer is not a homopolymer it can contain spacer non-cationic monomer units. Such polymers are described in the CTFA Cosmetic Ingredient Directory, 3rd edition. The ratio of the cationic to non-cationic monomer units is selected to give a polymer having a cationic charge density in the required range.

Suitable cationic conditioning polymers include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have C1–C7 alkyl groups, more preferably C1–3 alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition. In general secondary and tertiary amines, especially tertiary, are preferred.

Amine substituted vinyl monomers and amines can be polymerized in the amine form and then converted to ammonium by quaternization.

The cationic conditioning polymers can comprise mixtures of monomer units derived from amine- and/or quaternary ammonium-substituted monomer and/or compatible spacer monomers.

Suitable cationic conditioning polymers include, for example:

- copolymers of 1-vinyl-2-pyrrolidine and 1-vinyl-3-methyl-imidazolium salt (e.g. chloride salt), referred to in the industry by the Cosmetic, Toiletry, and Fragrance Association, (CTFA) as Polyquaternium-16. This material is commercially available from BASF Wyandotte Corp. (Parsippany, N.J., USA) under the LUVIQUAT tradename (e.g. LUVIQUAT FC 370);
- copolymers of 1-vinyl-2-pyrrolidine and dimethylaminoethyl methacrylate, referred to in the industry (CTFA) as Polyquaternium-11. This material is available commercially from Gaf Corporation (Wayne, N.J., USA) under the GAFQUAT tradename (e.g., GAFQUAT 755N);
- cationic diallyl quaternary ammonium-containing polymers including, for example, dimethyidiallyammonium chloride homopolymer and copolymers of acrylamide and dimethyldiallylammonium chloride, referred to in the industry (CTFA) as Polyquaternium 6 and Polyquaternium 7, respectively;
- mineral acid salts of amino-alkyl esters of homo-and co-polymers of unsaturated carboxylic acids having from 3 to 5 carbon atoms, (as described in U.S. Pat. No. 4,009,256);
- cationic polyacrylamides(as described in WO95/22311).

Other cationic conditioning polymers that can be used include cationic polysaccharide polymers, such as cationic cellulose derivatives, cationic starch derivatives, and cationic guar gum derivatives. Suitably, such cationic polysaccharide polymers have a charge density in the range from 0.1 to 4 meq/g.

Cationic polysaccharide polymers suitable for use in compositions of the invention include those of the formula:

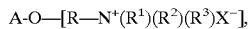

A-O—[R—N$^+$(R$^1$)(R$^2$)(R$^3$)X$^-$].

wherein: A is an anhydroglucose residual group, such as a starch or cellulose anhydroglucose residual. R is an alkylene, oxyalkylene, polyoxyalkylene, or hydroxyalkylene group, or combination thereof. R$^1$, R$^2$ and R$^3$ independently represent alkyl, aryl, alkylaryl, arylalkyl, alkoxyalkyl, or alkoxyaryl groups, each group containing up to about 18 carbon atoms. The total number of carbon atoms for each cationic moiety (i.e., the sum of carbon atoms in R$^1$, R$^2$ and R$^3$) is preferably about 20 or less, and X$^-$ is an anionic counterion. Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200.

Other suitable cationic polysaccharide polymers include quaternary nitrogen-containing cellulose ethers (e.g. as described in U.S. Pat. No. 3,962,418), and copolymers of etherified cellulose and starch (e.g. as described in U.S. Pat. No. 3,958,581).

A particularly suitable type of cationic polysaccharide polymer that can be used is a cationic guar gum derivative, such as guar hydroxypropyltrimonium chloride (commercially available from Rhone-Poulenc in their JAGUAR trademark series).

Examples are JAGUAR C13S, which has a low degree of substitution of the cationic groups and high viscosity. JAGUAR C15, having a moderate degree of substitution and a low viscosity, JAGUAR C17 (high degree of substitution, high viscosity), JAGUAR C16, which is a hydroxypropylated cationic guar derivative containing a low level of substituent groups as well as cationic quaternary ammonium groups, and JAGUAR 162 which is a high transparency, medium viscosity guar having a low degree of substitution.

Preferably the cationic conditioning polymer is selected from cationic cellulose and cationic guar derivatives. Particularly preferred cationic polymers are JAGUAR C13S, JAGUAR C15, JAGUAR C17 and JAGUAR C16 and JAGUAR C162.

The cationic conditioning polymer will generally be present in compositions of the invention at levels of from 0.01 to 5, preferably from 0.05 to 1, more preferably from 0.08 to 0.5 wt %.

Conditioning Agents

The compositions of this invention can also contain one or more conditioning agents selected from silicone conditioning agents and non-silicone oily conditioning agents.

When conditioning agent is present in the hair treatment compositions in droplet form, the droplets may be liquid, semi-solid or solid in nature, so long as they are substantially uniformly dispersed in the fully formulated product. Any droplets of oily conditioning agent are preferably present as either liquid or semi-solid droplets, more preferably as liquid droplets.

Silicone Conditioning Agents

The compositions of the invention can contain, emulsified droplets of a silicone conditioning agent, for enhancing conditioning performance. The silicone conditioning agent is insoluble in the aqueous matrix of the composition and so is present in an emulsified form, with the silicone present as dispersed droplets.

Suitable silicone conditioning agents include polydiorganosiloxanes, in particular polydimethylsiloxanes which have the CTFA designation dimethicone. Also suitable for use compositions of the invention (particularly shampoos and conditioners) are polydimethyl siloxanes having hydroxyl end groups, which have the CTFA designation dimethiconol. Also suitable for use in compositions of the invention are silicone gums having a slight degree of cross-linking, as are described for example in WO 96/31188. These materials can impart body, volume and stylability to hair, as well as good wet and dry conditioning.

The viscosity of the emulsified silicone conditioning agent itself (not the emulsion or the final hair conditioning composition) is typically at least 10,000 cst. In general we have found that conditioning performance increases with increased viscosity. Accordingly, the viscosity of the silicone conditioning agent itself is preferably at least 60,000 cst, most preferably at least 500,000 cst, ideally at least 1,000,000 cst. Preferably the viscosity does not exceed 109 cst for ease of formulation.

Emulsified silicone conditioning agents for use in the shampoo compositions of the invention will typically have an average silicone droplet size in the composition of less than 30, preferably less than 20, more preferably less than 10 $\mu$m. We have found that reducing the droplet size generally improves conditioning performance. Most preferably the average silicone droplet size of the emulsified silicone in the composition is less than 2 $\mu$m, ideally it ranges from 0.01 to 1 $\mu$m. Silicone emulsions having an average silicone droplet size of ±0.15 $\mu$m are generally termed microemulsions.

Suitable silicone emulsions for use in the invention are also commercially available in a pre-emulsified form.

Examples of suitable pre-formed emulsions include emulsions DC2-1766, DC2-1784, and microemulsions DC2-1865 and DC2-1870, all available from Dow Corning. These are all emulsions/microemulsions of dimethiconol. Cross-linked silicone gums are also available in a pre-emulsified form, which is advantageous for ease of formulation. A preferred example is the material available from Dow Corning as DC 2-1787, which is an emulsion of cross-linked dimethiconol gum. A further preferred example is the material available from Dow Corning as DC 2-1391, which is a microemulsion of cross-linked dimethiconol gum.

A further preferred class of silicone conditioning agents for inclusion in shampoos and conditioners of the invention are amino functional silicones. By "amino functional silicone" is meant a silicone containing at least one primary, secondary or tertiary amine group, or a quaternary ammonium group.

Examples of suitable amino functional silicones include:

(i) polysiloxanes having the CTFA designation "amodimethicone", and the general formula:

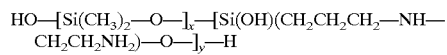

wherein x and y are numbers such that the molecular weight is between about 5,000 and 500,000.

(ii) polysiloxanes having the formula:

in which:

G is selected from H, phenyl, OH or $C_{1-8}$ alkyl, e.g. methyl;
a is 0 or an integer from 1 to 3, preferably 0;
b is 0 or 1, preferably 1;
m and n are numbers such that (m+n) can range from 1 to 2000, preferably from 50 to 150;
m is a number from 1 to 2000, preferably from 1 to 10;
n is a number from 0 to 1999, preferably from 49 to 149, and
R' is a monovalent radical of formula $-C_qH_{2q}L$ in which q is a number from 2 to 8 and L is an aminofuctional group selected from the following:

—NR"—CH$_2$—CH$_2$—N(R")$_2$
—N(R")$_2$
—N$^+$(R")$_3$A$^-$
—N$^+$H(R")$_2$A$^-$
—N$^+$H$_2$(R")A$^-$
—N(R")—CH$_2$—CH$_2$—N$^+$H$_2$(R")A$^-$ in which R" is selected from H, phenyl, benzyl, or a saturated monovalent hydrocarbon radical, e.g. $C_{1-20}$ alkyl, and A- is a halide ion, e.g. chloride or bromide.

Suitable amino functional silicones corresponding to the above formula include those polysiloxanes termed "trimethylsilylamodimethicone" as depicted below, and which are sufficiently water insoluble so as to be useful in compositions of the invention:

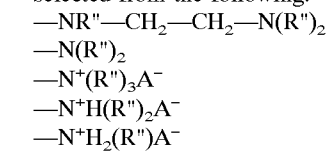

wherein x+y is a number from about 50 to about 500, and wherein R is an alkylene group having from 2 to 5 carbon atoms. Preferably, the number x+y is in the range of from about 100 to about 300.

(iii) quaternary silicone polymers having the general formula:

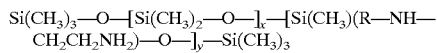

wherein $R^1$ and $R^{10}$ may be the same or different and may be independently selected from H, saturated or unsaturated long or short chain alk(en)yl, branched chain alk(en)yl and $C_5$–$C_8$ cyclic ring systems;

$R^2$ through $R^9$ may be the same or different and may be independently selected from H, straight or branched chain lower alk(en)yl, and $C_5$–$C_8$ cyclic ring systems;
n is a number within the range of about 60 to about 120, preferably about 80, and
X$^-$ is preferably acetate, but may instead be for example halide, organic carboxylate, organic sulphonate or the like.

Suitable quaternary silicone polymers of this class are described in EP-A-0 530 974.

Amino functional silicones suitable for use in shampoos and conditioners of the invention will typically have a mole % amine functionality in the range of from about 0.1 to about 8.0 mole %, preferably from about 0.1 to about 5.0 mole %, most preferably from about 0.1 to about 2.0 mole %. In general the amine concentration should not exceed about 8.0 mole % since we have found that too high an amine concentration can be detrimental to total silicone deposition and therefore conditioning performance.

The viscosity of the amino functional silicone is not particularly critical and can suitably range from about 100 to about 500,000 cSt.

Specific examples of amino functional silicones suitable for use in the invention are the aminosilicone oils DC2-8220, DC2-8166, DC2-8466, and DC2-8950-114 (all ex Dow Corning), and GE 1149-75, (ex General Electric Silicones).

Also suitable are emulsions of amino functional silicone oils with non ionic and/or cationic surfactant.

Suitably such pre-formed emulsions will have an average amino functional silicone droplet size in the shampoo composition of less than 30, preferably less than 20, more preferably less than 10 μm. Again, we have found that reducing the droplet size generally improves conditioning performance. Most preferably the average amino functional silicone droplet size in the composition is less than 2 μm ideally it ranges from 0.01 to 1 μm.

Pre-formed emulsions of amino functional silicone are also available from suppliers of silicone oils such as Dow Corning and General Electric. Specific examples include DC929 Cationic Emulsion, DC939 Cationic Emulsion, and the non-ionic emulsions DC2-7224, DC2-8467, DC2-8177 and DC2-8154 (all ex Dow Corning).

An example of a quaternary silicone polymer useful in the present invention is the material K3474, ex Goldschmidt.

For shampoo compositions according to the invention intended for the treatment of "mixed" hair (i.e. greasy roots and dry ends), it is particularly preferred to use a combination of amino functional and non-amino functional silicone in compositions of the invention, especially when these are in the form of shampoo compositions. In such a case, the weight ratio of amino functional silicone to non-amino functional silicone will typically range from 1:2 to 1:20, preferably 1:3 to 1:20, more preferably 1:3 to 1:8.

The total amount of silicone incorporated into compositions of the invention depends on the level of conditioning desired and the material used. A preferred amount is from 0.01 to 10 wt % although these limits are not absolute. The lower limit is determined by the minimum level to achieve conditioning and the upper limit by the maximum level to avoid making the hair and/or skin unacceptably greasy.

We have found that a total amount of silicone of from 0.3 to 5, preferably 0.5 to 3 wt % is a suitable level.

The viscosity of silicones and silicone emulsions can be measured by means of a glass capillary viscometer as set out further in Dow Corning Corporate Test Method CTM004, Jul. 20 1970.

In compositions comprising silicone conditioning agent, it is preferred that a suspending agent for the silicone conditioning agent also be present. Suitable suspending agents are as described hereinabove.

Non-Silicone Oily Conditioning Components

Compositions according to the present invention may also comprise a dispersed, non-volatile, water-insoluble oily conditioning agent.

This component will be dispersed in the composition in the form of droplets, which form a separate, discontinuous phase from the aqueous, continuous phase of the composition. In other words, the oily conditioning agent will be present in the shampoo composition in the form of an oil-in-water emulsion.

Suitably, the $D_{3,2}$ average droplet size of the oily conditioning component is at least 0.4, preferably at least 0.8, and more preferably at least 1 μm. Additionally, the $D_{3,2}$ average droplet size of the oily conditioning component is preferably no greater than 10, more preferably no greater 8, more preferably no greater than 5, yet more preferably no greater than 4, and most preferably no greater than 3.5 μm.

The oily conditioning agent may suitably be selected from oily or fatty materials, and mixtures thereof.

Oily or fatty materials are preferred conditioning agents in the shampoo compositions of the invention for adding shine to the hair and also enhancing dry combing and dry hair feel.

Preferred oily and fatty materials will generally have a viscosity of less than 5 Pa.s, more preferably less than 1 Pa.s, and most preferably less than 0.5 Pa.s, e.g. 0.1 Pa.s and under as measured at 25° C. with a Brookfield Viscometer (e.g. Brookfield RV) using spindle 3 operating at 100 rpm.

Oily and fatty materials with higher viscosities may be used. For example, materials with viscosities as high as 65 Pa.s may be used. The viscosity of such materials (i.e. materials with viscosities of 5 Pa.s and greater) can be measured by means of a glass capillary viscometer as set out further in Dow Corning Corporate Test Method CTM004, Jul. 20 1970.

Suitable oily or fatty materials are selected from hydrocarbon oils, fatty esters and mixtures thereof.

Hydrocarbon oils include cyclic hydrocarbons, straight chain aliphatic hydrocarbons (saturated or unsaturated), and branched chain aliphatic hydrocarbons (saturated or unsaturated). Straight chain hydrocarbon oils will preferably contain from about 12 to about 30 carbon atoms. Branched chain hydrocarbon oils can and typically may contain higher numbers of carbon atoms. Also suitable are polymeric hydrocarbons of alkenyl monomers, such as $C_2$–$C_6$ alkenyl monomers. These polymers can be straight or branched chain polymers. The straight chain polymers will typically be relatively short in length, having a total number of carbon atoms as described above for straight chain hydrocarbons in general. The branched chain polymers can have substantially higher chain length. The number average molecular weight of such materials can vary widely, but will typically be up to about 2000, preferably from about 200 to about 1000, more preferably from about 300 to about 600.

Specific examples of suitable hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, and mixtures thereof. Branched-chain isomers of these compounds, as well as of higher chain length hydrocarbons, can also be used. Exemplary branched-chain isomers are highly branched saturated or unsaturated alkanes, such as the permethyl-substituted isomers, e.g., the permethyl-substituted isomers of hexadecane and eicosane, such as 2, 2, 4, 4, 6, 6, 8, 8-dimethyl-10-methylundecane and 2, 2, 4, 4, 6, 6-dimethyl-8-methylnonane, sold by Permethyl Corporation. A further example of a hydrocarbon polymer is polybutene, such as the copolymer of isobutylene and butene. A commercially available material of this type is L-14 polybutene from Amoco Chemical Co. (Chicago, Ill., U.S.A.).

Particularly preferred hydrocarbon oils are the various grades of mineral oils. Mineral oils are clear oily liquids obtained from petroleum oil, from which waxes have been removed, and the more volatile fractions removed by distillation. The fraction distilling between 250° C. to 300° C. is termed mineral oil, and it consists of a mixture of hydrocarbons ranging from $C_{16}H_{34}$ to $C_{21}H_{44}$. Suitable commercially available materials of this type include Sirius M85 and Sirius M125, all available from Silkolene.

Suitable fatty esters are characterized by having at least 10 carbon atoms, and include esters with hydrocarbyl chains derived from fatty acids or alcohols, e.g., monocarboxylic acid esters, polyhydric alcohol esters, and di- and tricarboxylic acid esters. The hydrocarbyl radicals of the fatty esters hereof can also include or have covalently bonded thereto other compatible functionalities, such as amides and alkoxy moieties, such as ethoxy or ether linkages.

Monocarboxylic acid esters include esters of alcohols and/or acids of the formula R'COOR in which R' and R independently denote alkyl or alkenyl radicals and the sum of carbon atoms in R' and R is at least 10, preferably at least 20.

Specific examples include, for example, alkyl and alkenyl esters of fatty acids having aliphatic chains with from about 10 to about 22 carbon atoms, and alkyl and/or alkenyl fatty alcohol carboxylic acid esters having an alkyl and/or alkenyl alcohol-derived aliphatic chain with about 10 to about 22 carbon atoms, benzoate esters of fatty alcohols having from about 12 to 20 carbon atoms.

The monocarboxylic acid ester need not necessarily contain at least one chain with at least 10 carbon atoms, so long as the total number of aliphatic chain carbon atoms is at least 10. Examples include isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, and oleyl adipate.

Di- and trialkyl and alkenyl esters of carboxylic acids can also be used. These include, for example, esters of $C_4$–$C_8$ dicarboxylic acids such as $C_1$–$C_{22}$ esters (preferably $C_1$–$C_6$) of succinic acid, glutaric acid, adipic acid, hexanoic acid, heptanoic acid, and octanoic acid. Examples include diisopropyl adipate, diisohexyl adipate, and diisopropyl sebacate. Other specific examples include isocetyl stearoyl stearate, and tristearyl citrate.

Polyhydric alcohol esters include alkylene glycol esters, for example ethylene glycol mono and di-fatty acid esters, diethylene glycol mono- and di-fatty acid esters, polyethylene glycol mono- and di-fatty acid esters, propylene glycol mono- and di-fatty acid esters, polypropylene glycol monooleate, polypropylene glycol monostearate, ethoxylated propylene glycol monostearate, polyglycerol polyfatty acid esters, ethoxylated glyceryl monostearate, 1,3-butylene glycol monostearate, 1,3-butylene glycol distearate, polyoxyethylene polyol fatty acid ester, sorbitan fatty acid esters, polyoxyethylene sorbitan fatty acid esters and mono-, di-and triglycerides.

Particularly preferred fatty esters are mono-, di- and triglycerides, more specifically the mono-, di-, and tri-esters of glycerol and long chain carboxylic acids such as $C_1$–$C_{22}$ carboxylic acids. A variety of these types of materials can be obtained from vegetable and animal fats and oils, such as coconut oil, castor oil, safflower oil, sunflower oil, cottonseed oil, corn oil, olive oil, cod liver oil, almond oil, avocado oil, palm oil, sesame oil, peanut oil, lanolin and soybean oil. Synthetic oils include triolein and tristearin glyceryl dilaurate.

Specific examples of preferred materials include cocoa butter, palm stearin, sunflower oil, soyabean oil and coconut oil.

The oily or fatty material is suitably present at a level of from 0.05 to 10, preferably from 0.2 to 5, more preferably from about 0.5 to 3 wt %.

The compositions of this invention preferably contain no more than 3 wt % of a styling polymer, more preferably less than 1% of a styling polymer, preferably contain less than 0.1% by weight a styling polymer, and optimally are free of styling polymer.

In hair treatment compositions containing a conditioning agent, it is preferred that a cationic polymer also be present.

Adjuvants

The compositions of the present invention may also contain adjuvants suitable for hair care. Generally such ingredients are included individually at a level of up to 2, preferably up to 1 wt % of the total composition.

Among suitable hair care adjuvants, are:

(i) natural hair root nutrients, such as amino acids and sugars. Examples of suitable amino acids include arginine, cysteine, glutamine, glutamic acid, isoleucine, leucine, methionine, serine and valine, and/or precursors and derivatives thereof. The amino acids may be added singly, in mixtures, or in the form of peptides, e.g. di- and tripeptides. The amino acids may also be added in the form of a protein hydrolysate, such as a keratin or collagen hydrolysate. Suitable sugars are glucose, dextrose and fructose. These may be added singly or in the form of, e.g. fruit extracts. A particularly preferred combination of natural hair root nutrients for inclusion in compositions of the invention is isoleucine and glucose. A particularly preferred amino acid nutrient is arginine.

(ii) hair fibre benefit agents. Examples are:

ceramides, for moisturizing the fibre and maintaining cuticle integrity. Ceramides are available by extraction from natural sources, or as synthetic ceramides and pseudoceramides. A preferred ceramide is Ceramide II, ex Quest. Mixtures of ceramides may also be suitable, such as Ceramides LS, ex Laboratoires Serobiologiques.

The invention will now be further illustrated by the following, non-limiting Examples.

TABLE 1

| Ingredient | Example 1 Weight % | Example 2 Weight % | Example 3 Weight % | Example 4 Weight % | Example 5 Weight % | Example 6 Weight % |
|---|---|---|---|---|---|---|
| Stearamidopropyl dimethylamine, | 0.750 | 0.750 | 0.750 | 0.750 | 0.750 | 0.750 |
| PEG-2 oleamonium chloride & propylene glycol | 2.000 | 2.000 | 2.000 | 2.000 | 2.000 | 2.000 |
| Behentrimonium Methosulfate and cetearyl alcohol | 0.25 | 1.000 | 1.000 | 1.000 | 1.000 | 1.000 |
| Cetyl alcohol | 3.000 | 3.000 | 3.000 | 3.000 | 3.000 | 3.000 |
| Stearyl alcohol | 2.000 | 2.000 | 2.000 | 2.000 | 2.000 | 2.000 |
| Disodium EDTA | 0.100 | 0.100 | 0.100 | 0.100 | 0.100 | 0.100 |
| Dimethiconol | 0.000 | 0.000 | 0.000 | 0.000 | 0.8 | 0.000 |
| Silicone fluid 245 | 0.000 | 0.000 | 0.000 | 0.000 | 2.000 | 0.000 |
| Fragrance | 0.600 | 0.600 | 0.600 | 0.600 | 0.600 | 0.600 |
| Low Tack Silicone PSA emulsion[1] | 0.000 | 0.2 | 0.4 | 0.4 | 0.000 | 0.000 |
| Colloidal silica | 0.5 | 0.000 | 0.000 | 0.000 | 0.000 | 0.000 |
| Water, fragrance, preservatives | q.s. | q.s | q s. | q.s | q.s. | q.s. |
| Total | 100.00 | 100.00 | 100.00 | 100.00 | 100.00 | 100.00 |

[1]Low Tack Silicone PSA emulsion is available from Dow Corning Corp. (DC 5-7300) which is a 40% emulsion of silicone PSA that contains 65% silicone resin and 35% silicone polymer.

TABLE 2

| Ingredient | Example 7 Weight % | Example 8 Weight % | Example 9 Weight % | Example 10 Weight % | Example 11 Weight % |
|---|---|---|---|---|---|
| Water, soft | 45.000 | 45.000 | 45.000 | 45.000 | 45.000 |
| Hydroxyethylcellulose | 0.200 | 0.000 | 0.000 | 0.000 | 0.200 |
| Cetrimonium Chloride | 2.800 | 2.500 | 2.500 | 2.500 | 2.800 |
| Quaternium-18 and propylene glycol | 0.500 | 0.400 | 0.400 | 0.400 | 0.500 |
| Cetyl/Stearyl alcohol | 3.000 | 3.000 | 3.000 | 3.000 | 3.000 |
| Disodium EDTA, 100% active | 0.100 | 0.100 | 0.100 | 0.100 | 0.100 |
| Dimethiconol | 0.8 | 0.6 | 0.6 | 0.6 | 0.8 |
| Silicone fluid 245 | 0.000 | 0.000 | 0.000 | 0.000 | 0.000 |
| Fragrance | 0.400 | 0.400 | 0.600 | 0.600 | 0.600 |
| Low Tack Silicone PSA emulsion[1] | 0.000 | 0.000 | 0.000 | 0.500 | 0.000 |
| Water, Fragrance, Preservative | q.s. | q.s. | q.s. | q.s. | q.s. |
| Total | 100.000 | 100.000 | 100.000 | 100.000 | 100.000 |

Measurement of Static and Dynamic Friction

Friction measurements are performed using a modified version of a previously described methodology based on Dynamic Mechanical Analysis (DMA) (Ref: U.S. Pat. No. 5,968,286 which is hereby incorporated by reference). Testing involves the application of different force profiles to a bundle of hair fibers. One manner for carrying out testing involves using a single cantilever geometry wherein only one side of a hair bundle is secured. The extent to which the bundle deflects under force will possess a dependance on the interfiber friction. As such, relative differences in the frictional properties of hair can be measured by comparing the results from treated and untreated hair bundles. A diagram of the experimental set up is shown below in FIG. 1.

Figure 2:
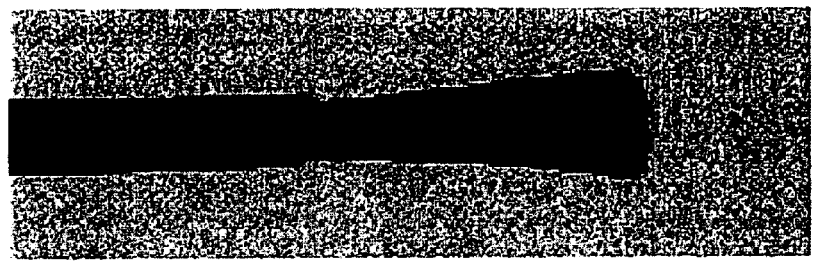
FIG. 2 is a close-up view of a hair sample held by a positioning tube employed with the test instrument of FIG. 1.

Two-gram hair tresses are prepared using natural brown hair purchased from Imhair Ltd.(Italy). Before testing, all tresses are cleaned thoroughly using standard surfactant solutions. Each tress is cut to the length of 6 inches. Testing is performed with the hair encased in a thin-walled latex tube with an inside diameter of 3 mm, and outside diameter 3.4 mm. A close up of the hair and the tube is shown in FIG. 2.

For statistical purposes, 4 tube samples are tested for each formulation. Testing is first performed on an untreated hair array. After testing, the hair is removed from the latex tube and treated with the test formula. The formula is applied in the proportion 0.2 ml to 2 g of hair for a shampoo, and 0.3 ml to 2 g of hair for a conditioner product. Each hair array is treated for 1 minute and then rinsed for 30 seconds in warm water (40° C.), at a flow rate of 2 l/min. After treatment the arrays are air dried for 24 hours at 30% RH, and a temperature of 20° C. The samples are then placed back in the latex tube and equilibrated for the next 24 hours under the same conditions. The treated hair arrays are then tested again to allow for differences in deflection to be observed as a result of surface modification imparted by the test material.

A Perkin Elmer DMA 7e housed within an environmentally controlled chamber is used for all our measurements. The tube sample is mounted in the single cantilever DMA fixture in such a way that the length of the latex tube protruding from the clamp is 20 mm (see FIG. 1). The instrument probe imposes a bending force on the top of the tube at a distance of 7.5 mm from the clamp.

By imposing different force profiles, it is possible to measure different frictional properties of the hair. For example, a measure of the static friction can be obtained by performing a test in which the bending force is gradually increased. Meanwhile, the dynamic friction is measured by imposing an oscillating sinusoidal force. In each case, the instrument measures the resulting deflection or strain that results in the specimen. More detailed information regarding these two modes of operation are given below.

Change in Static Friction

The coefficient of static friction is calculated from a test in which an increasing bending force deflects the tube sample. Initially, the process is elastic and consequently a linear relationship exists between the stress (force/unit area) and the deflection. Under these conditions the array behaves like a solid rod, since the interfiber friction and the external pressure of the tube holds the fibers together and prevents movement of the individual fibers. However, at a certain critical force, adjacent fibers will start to slide over one another. As the result of this interfiber slip, the total resistance of the sample towards the bending force decreases. From this point on, the deflection increases faster than the bending stress. That is, the linear relationship between the stress and strain is lost. The critical deflection d. at which the interfiber slip appears is measured by the instrument and can be used to calculate an average coefficient of internal static friction in the tube sample. The change in static friction is calculated by comparing the critical deflection of the same hair array before and after treatment with the test sample.

Change in Dynamic Friction

The dynamic friction test is somewhat more complex. The use of an oscillating force allows for the deconvolution of a material's elastic (storage) and viscous (lost) components. These quantities identify the ability of the material to recover from deformation (elasticity) or to dissipate a portion of the mechanical energy (damping). Friction is a property that is associated with the dissipation of the mechanical energy and therefore can be probed using the loss component that is obtained from a dynamic mechanical test.

Figure 3:
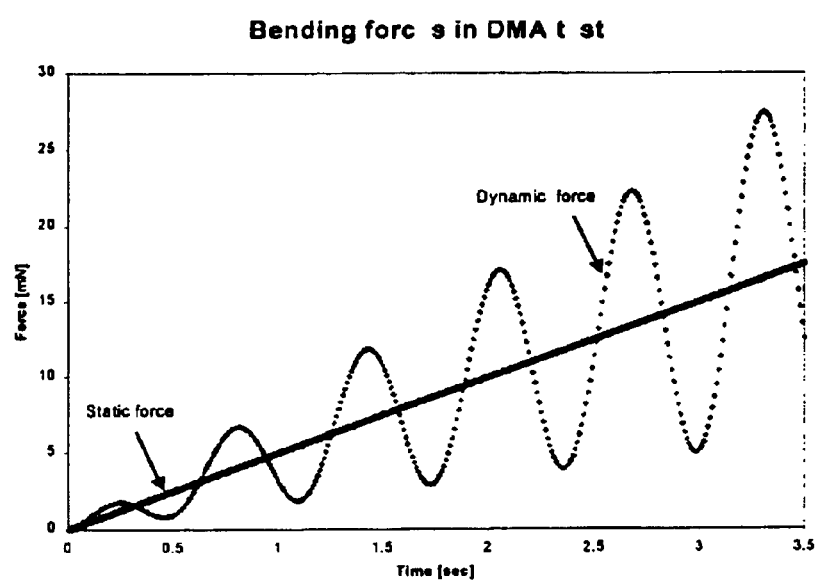
FIG. 3 is a graph schematically illustrating the behavior of dynamic force superimposed over a gradually increasing static force as measured in the test equipment of FIG. 1.

Dynamic friction testing is performed by introducing a gradually increasing dynamic force to the sample at a constant frequency. Furthermore, this dynamic force is superimposed over a gradually increasing static force. This behavior is shown schematically in FIG. 3.

Calculation of the coefficient of dynamic friction is more complex and requires a detailed analysis involving the movement of the fiber bundle as a result of the two superimposed bending forces. As the magnitude of both the static and dynamic force is raised, so the magnitude of the deflection also increases. That is, the amplitude of dynamic bending also increases. Furthermore, the magnitude of the bending amplitude is influenced by the surface frictional properties of the hair fibers. The measurement of the amplitude before and after the treatment allows for assessment of a relative change in dynamic friction Δfd.

The relative coefficient of dynamic friction is calculated by:

$$\Delta fd/fd = (A_U - A_T)/A_U$$

where $A_U$ is the maximum amplitude of bending before treatment, and $A_T$ is the maximum amplitude for the same hair array after the treatment.

Figure 4:
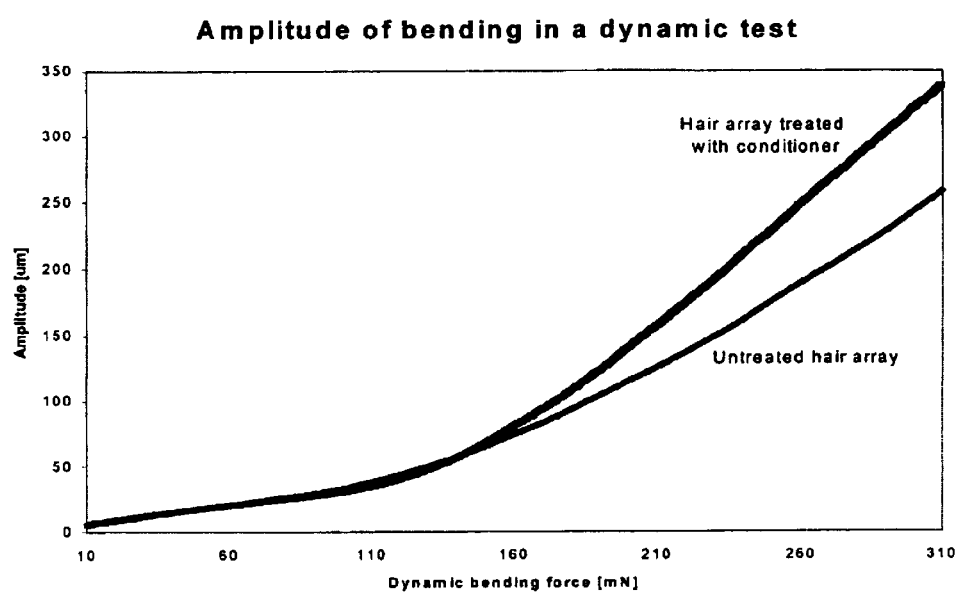
FIG. 4 is a graph illustrating the dynamic bending force as measured by the test equipment outlined in FIG. 1.

If the same hair array were treated with a conditioning formula that reduces the surface friction, then the same bending force would be able to generate longer interfiber slip and the higher amplitude of bending (FIG. 4). The results of frictional tests are valid only for the treatments, which do not change the bulk properties of hair fibers, but only their surface friction.

The experimental data below demonstrates the beneficial properties of compositions of the invention.

Table 3 includes the static and dynamic friction properties as measured by the above mentioned DMA technique for the formulation examples as listed in tables 1 and 2.

TABLE 3

| Conditioner Description | Static Friction (%) | Dynamic Friction (%) |
| --- | --- | --- |
| Example 1 | 210 | 280 |
| Example 2 | 17 | 3 |
| Example 3 | 31 | 5 |
| Example 4 | 45 | 26 |
| Example 5 | 30 | 2 |
| Example 6 | −21 | −29 |
| Example 7 | −10 | −31 |
| Example 8 | 25 | −11 |
| Example 9 | −17.67 | −22.67 |
| Example 10 | 24 | 25 |
| Example 11 | −16 | −29 |

Shampoo Compositions

The invention will now be further illustrated by the following, non-limiting example 12 of a shampoo formulation.

TABLE 4

| Ingredient | Example 12 Weight % | Example 13 Weight % |
| --- | --- | --- |
| Emulsion stabilizer | 0.400 | 0.400 |
| Ammonium Lauryl Sulphate | 7.605 | 7.605 |
| Ammonium Laureth Sulphate | 5.941 | 5.941 |
| Cocamide MEA | 1.300 | 1.300 |
| PEG-6 Cocamide | 0.650 | 0.650 |
| Propylene Glycol | 0.500 | 0.500 |
| Guar Hydroxypropyltrimonium chloride | 0.100 | 0.100 |
| Dimethiconol | 1.000 | 1.000 |
| Low Tack Silicone PSA[1] | 0.000 | 0.750 |
| Chelating agent | 0.080 | 0.080 |
| Water, Fragrance, and Preservatives | q.s. | q.s. |

Table 5 includes the static and dynamic friction properties as measured by the above mentioned DMA technique for the formulation examples as listed in tables 4.

TABLE 5

| Shampoo Description | Static Friction (%) | Dynamic Friction (%) |
| --- | --- | --- |
| Example 12 | −7 | −11 |
| Example 13 | 18 | 3 |

Suspension Composition:

The invention will now be further illustrated by the following, non-limiting example of a suspension.

| Example 14 | |
| --- | --- |
| Description | Wt. % |
| Silicone PSA emulsion[1] (40% active) | 2.00 |
| Carbopol 980, 100% active | 1.00 |
| DMDM Hydantoin | 0.1 |
| Kathon CG, 39% active | 0.04 |
| Soft water, 100% active | 96.86 |
| Total | 100.00 |

What is claimed is:

1. An aqueous hair treatment composition comprising:
   a) at least one silicone pressure sensitive adhesive comprising a hydroxy-terminated polydimethylsiloxane gum of Tg below −20° C. cross-linked with a silicone resin of Tg above 0° C., the gum to resin being present in a ratio from 25:75 to 75:25, the silicone pressure sensitive adhesive being other than a silicone acrylate copolymer; and
   b) a hair conditioning agent selected from the group consisting of cationic surfactants and cationic polymers.

2. An aqueous hair treatment composition according to claim 1 wherein said composition increases static friction of dry hair by at least about 10%, and wherein said composition increases dynamic friction of dry hair by no more than about 100% or decreases or leaves unchanged said dynamic friction.

3. An aqueous hair treatment composition according to claim 2 wherein said composition increases dynamic friction of dry hair by no more than about 60%.

4. An aqueous hair treatment composition according to claim 2 wherein said composition increases dynamic friction of dry hair by no more than about 40%.

5. An aqueous hair treatment composition according to claim 2 wherein said composition increases static friction of dry hair by at least about 15%.

6. An aqueous hair treatment composition according to claim 2 wherein said composition increases static friction of dry hair by at least about 20%.

7. A composition in accordance with claim 1, wherein said silicone pressure sensitive adhesive is the product of mixing 30 to 60 parts by weight of a silanol-terminated polydiorganosiloxane of Tg below −20° C. and viscosity 0.1–30000 Pa.s at 25° C. lightly crosslinked with 40 to 70 parts by weight of a silanol-containing silicone resin of Tg above 0° C. comprising monovalent trihydrocarbonsiloxy (M) groups of the formula $R''_3SiO_{1/2}$ and tetrafunctional (Q) groups $SiO_{4/2}$ wherein R" denotes a monovalent hydrocarbon group having 1 to 6 carbon atoms, the number ratio of M groups to Q groups being in the range 0.5:1 to 1.2:1.

8. A composition in accordance to claim 1, wherein said pressure sensitive adhesive is dispersed as an emulsion comprising a disperse silicone phase emulsified in a continuous water phase in the presence of a surfactant, wherein the disperse silicone phase comprises 40 to 80% by weight of a silicone pressure sensitive adhesive, which is the lightly crosslinked product of mixing a silanol-terminated polydiorganosiloxane of Tg below −20° C. with a silanol-containing silicone resin of Tg above 0° C., dispersed in 60 to 20% by weight of a volatile silicone fluid having a boiling point below 300° C., the emulsion being substantially free of any non-silicon-containing volatile organic material.

9. An aqueous hair treatment composition according to claim 1 wherein the silicone pressure sensitive adhesive is present in an amount from about 0.01% to about 10% and the hair conditioning agent is present in an amount from about 0.05% to about 10%.

10. An aqueous hair treatment composition according to claim 1 which is a leave-in composition.

11. An aqueous hair treatment composition according to claim 1 which is a rinse-out composition.

12. A composition according to claim 1 which comprises a conditioning agent selected from the group consisting of: octyltrimethylammonium chloride, dodecyltrimethylammonium chloride, hexadecyltrimethylammonium chloride, cetyltrimethylammonium chloride, octyldimethylbenzylammonium chloride, decyldimethylbenzylammonium chloride, stearyldi-methylbenzylammonium chloride, didodecyldimethylammonium chloride, dioctadecyldimethylammonium chloride, tallow trimethylammonium chloride, cocotrimethylammonium chloride, Cetylpyridinium chloride, Quaternium-5 Quatemium-31 Quatemium-18; and mixtures thereof.

13. A composition in accordance with claim 1 which further comprises a suspending agent selected from the group consisting of polyacrylic acids; cross-linked polymers of acrylic acid; copolymers of acrylic acid with a hydrophobic monomer; copolymers of carboxylic acid-containing monomers and acrylic esters; cross-linked copolymers of acrylic acid and acrylate esters; heteropolysaccharide gum; ethylene glycol stearate; alkanolamides of fatty acids; ethylene glycol distearate; polyethylene glycol 3 distearate; Carbopol 420, Carbopol 488; Carbopol 493; Carbopol 910; Carbopol 934; Carbopol 940; Carbopol 941; Carbopol 980; Carbopol 1342; cross-linked polymers of acrylic acid and acrylate ester; xanthan gum and mixtures thereof.

14. A composition in accordance with claim 1 which is a shampoo and which comprises a hair cleansing agent selected from the group consisting of an anionic surfactant, a non-ionic surfactant, an amphoteric surfactant, and mixtures thereof.

15. A composition in accordance with claim 13 wherein said hair cleansing agent is selected from the group consisting of sodium dodecylbenzene sulphonate; sodium lauryl sulphate; sodium lauryl ether sulphate nEO, where n is from 1 to 20; octylphenol ether sulphate nEO where n is from 1 to 20; sodium dioctylsulphosuccinate; nonylphenol ethoxylate nEO, where n is from 1 to 50; alcohol ethoxylates; lauryl alcohol nEO, where n is from 1 to 50; and polyoxyethylene monostearate where the number of oxyethylene units is from 1 to 30.

16. A composition in accordance with claim 1, which further comprises a silicone conditioning agent selected from the group consisting of a volatile silicone, a nonvolatile silicone, and mixtures thereof.

* * * * *